United States Patent
Gasco et al.

(10) Patent No.: US 7,611,733 B2
(45) Date of Patent: Nov. 3, 2009

(54) NANOPARTICLE FORMULATIONS OF PLATINUM COMPOUNDS

(75) Inventors: Maria Rosa Gasco, Turin (IT); Paolo Gasco, Turin (IT); Alberto Bernareggi, Concorezzo (IT)

(73) Assignees: Cell Therapeutics Europe S.r.l. (IT); NANOVECTOR S.r.l. (IT)

( * ) Notice: Subject to any disclaimer, the term of this patent is extended or adjusted under 35 U.S.C. 154(b) by 0 days.

(21) Appl. No.: 10/594,003

(22) PCT Filed: Mar. 24, 2005

(86) PCT No.: PCT/EP2005/003186

§ 371 (c)(1),
(2), (4) Date: Jun. 5, 2007

(87) PCT Pub. No.: WO2005/092298

PCT Pub. Date: Oct. 6, 2005

(65) Prior Publication Data

US 2008/0038371 A1  Feb. 14, 2008

Related U.S. Application Data

(60) Provisional application No. 60/556,754, filed on Mar. 26, 2004.

(51) Int. Cl.
*A61K 9/26* (2006.01)
*A61K 31/28* (2006.01)
*C07F 15/00* (2006.01)

(52) U.S. Cl. .................. 424/649; 556/137; 514/492; 977/717; 977/911

(58) Field of Classification Search ............ 556/137; 514/492; 424/649; 977/717, 911
See application file for complete search history.

(56) References Cited

U.S. PATENT DOCUMENTS

| 5,250,236 A | 10/1993 | Gasco |
| 6,011,166 A * | 1/2000 | Valsecchi et al. ............ 556/137 |
| 6,287,593 B2 * | 9/2001 | Cherian ...................... 424/450 |
| 6,596,889 B1 * | 7/2003 | Menta et al. ................. 556/137 |

FOREIGN PATENT DOCUMENTS

| WO | WO-94/20072 A | 9/1994 |
| WO | WO-93/05768 A | 4/1996 |

OTHER PUBLICATIONS

Egea et al., "Penetration kinetics of cis-diaminedichloroplatinum(II) loaded nanoparticles in lipid monolayers as a membrane model of the reticuloendothelial system", Thin Solid Films, vol. 210/211, pp. 364-367, 1992.

\* cited by examiner

*Primary Examiner*—Porfirio Nazario Gonzalez
(74) *Attorney, Agent, or Firm*—Lerner, David, Littenberg, Krumholz & Mentlik, LLP

(57) ABSTRACT

Solid Lipid Nanoparticles of platinum compounds, particularly of antitumor platinum complexes are disclosed. The Nanoparticles of the invention are obtained by a process comprising: a) preparing a first microemulsion by mixing a molten lipid, a surfactant, and optionally a co-surfactant and the platinum compound acqueous solution; b) preparing a solution by mixing a surfactant and optionally a co-surfactant in water, heating to complete solution, preferably at the same melting temperature of the lipid used in a) and adding a co-surfactant; c) dispersing the microemulsion obtained in a) into the solution obtained in b) obtaining a multiple microemulsion c); d) dispersing the microemulsion obtained in c) in aqueous medium at a temperature ranging from 0.5° C. to 4° C. obtaining a dispersion of solid lipid microspheres; e) washing with aqueous medium through ultrafiltration the obtained lipid microspheres obtained in d) and lyophilizing, optionally in the presence of a bulking agent and of a cryoprotecting agent.

14 Claims, No Drawings

NANOPARTICLE FORMULATIONS OF PLATINUM COMPOUNDS

CROSS REFERENCE TO RELATED APPLICATIONS

The present application is a national phase entry under 35 U.S.C. §371 of International Application PCT/EP2005/003186, filed Mar. 24, 2005, published in English, which claims benefit of U.S. Provisional Patent Application 60/556,754, filed Mar. 26, 2004. The disclosures of all of said applications are incorporated by reference herein.

BACKGROUND OF THE INVENTION

Solid lipid nanoparticles or microparticles (SLNs or SLMs) or nanospheres are lipid particles having an average diameter smaller than one micron and usually in the range from some hundreds to a few nanometers, which have been thoroughly studied as carriers for controlled drug delivery. SLNs may be prepared by a number of methods from solid lipids, including e.g. high pressure homogenization (EP 605497) and via microemulsions (U.S. Pat. No. 5,250,236).

Reviews of the preparation as well as of the pharmaceutical applications of SLNs are reported for instance in Eur. J. Pharmaceutics and Biopharmaceutics, 50 (2000), 161-177, and in Pharm. Technol. Eur. 13 (2001) 32-42.

Pharmaceutical compositions in form of SLMs suitable for parenteral administration of drugs are particularly disclosed in EP 988031. Said formulations are characterized by specific compounds such as fatty acids, PEG-stearate, dipalmitoylphosphatidylethanolamine-PEG and the like, which stabilize said microparticles avoiding phagocytosis.

Microparticles particularly suited for drug delivery across mucosal tissues and the blood-brain barrier are disclosed in WO 99/27918 and U.S. Pat. No. 6,419,949. A number of medicaments including antibiotics, hormones and antitumor agents of different kinds are specifically cited.

Platinum compounds are among the most effective anticancer drugs used to treat solid tumors. After intravenous administration, platinum species tend to bind irreversibly to plasma proteins (covalent binding) in a time dependent kinetic, with more than 90% drug bound within a few hours from administration. Furthermore, for some new platinum complexes the fraction of drug that is free in plasma water and that is reversibly bound to plasma protein seems to undergo a progressive and rapid degradation to form inactive de-platinated species. These species are likely to be generated because of platinum compound chemical instability in plasma, possibly due to the interaction with nucleophilic thiol-containing endogenous molecules (e.g. cysteine residues, glutathione). The high degree of plasma protein binding in humans probably favors such interaction. Both the high irreversible binding to plasma protein and the fast degradation in human plasma may hamper platinum compounds efficacy in clinical trials.

DESCRIPTION OF THE INVENTION

It has now been found that platinum compounds having antitumor activity can be advantageously formulated into SLNs or SLMs, surprisingly improving the therapeutic index thereof.

According to the present invention, preferred platinum compounds include platinum complexes wherein the platinum metal atom is chelated by suitable ligands, particularly anionic ligands and ligands containing amino groups.

Preferred compounds are described in U.S. Pat. Nos. 6,022,892, 6,060,616, 5,744,497, 6,011,166, and 6,596,889.

Particularly preferred compounds are:

trans-{bis[trans(diammine)(chloro)platinum (II)(μ-1,6-hexanediamine)]}diammineplatinum tetranitrate salt of formula I, described in the Example 6 of U.S. Pat. No. 5,744,497:

Formula I

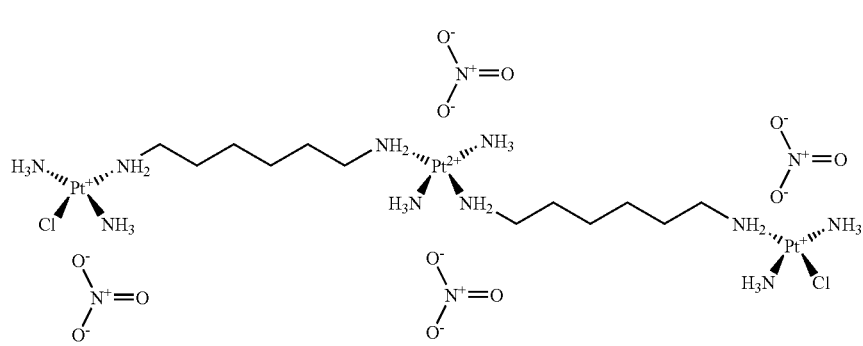

bis{trans(diammine)(chloro)platinum(II)}μ(1,16-diamino-7,10-diazahexadecane-N1,N16) dinitrate salt. 2HNO$_3$ of formula II, described in Example 17, page 15, line 25-31 of U.S. Pat. No. 6,022,892:

Formula II

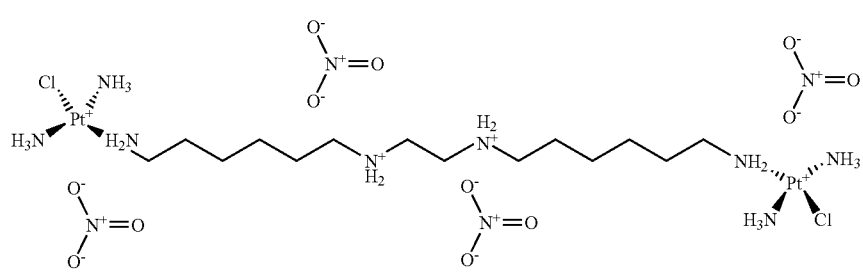

bis{trans(diammine)(chloro)platinum(II)}μ-(1,16-di-amino-6,11-diazahexadecane-N1,N16) dinitrate salt. 2HNO$_3$ of formula III, described in Example 17, page 15, line 32-38 of U.S. Pat. No. 6,022,892

Formula III

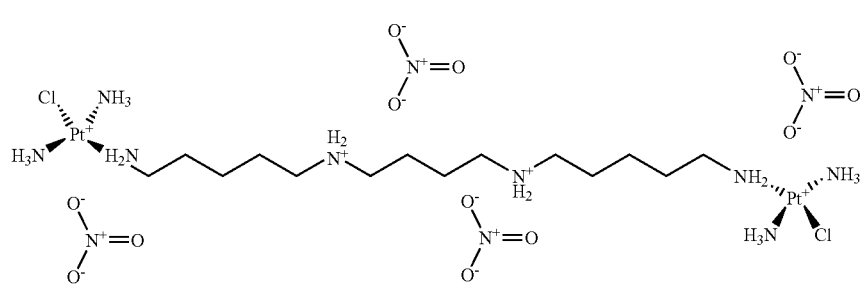

bis{trans(diammine)(chloro)platinum(II)}μ-(1,12-di-amino-4,9-diazadodecane-N$^1$,N$^2$) dinitrate salt. 2HNO$_3$ of formula IV, described in Example 2 of U.S. Pat. No. 6,596,889:

Formula IV

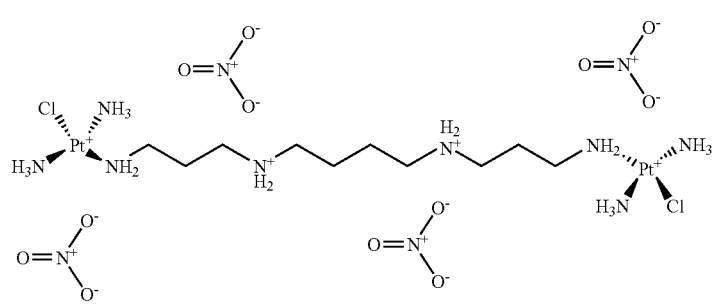

bis{trans(diammine)(chloro)platinum (II)}-μ-(1,8-di-amino-4-azaoctane-N$^1$,N$^8$) dinitrate salt. HNO$_3$ of formula V, described in Example 1 of U.S. Pat. No. 6,596,889:

Formula V

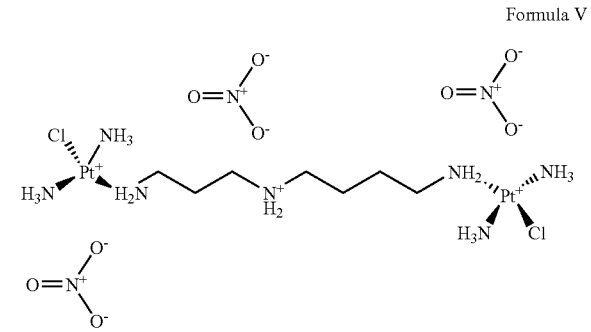

Solid Lipid Nanoparticle (SLN) formulations of platinum compounds can be obtained using solid lipids, surfactants and co-surfactants as excipients, using any of the methods disclosed in the above mentioned patent documents, which are herein incorporated by reference.

The nanoparticles of platinum compounds are obtained from warm microemulsions using the technology described (U.S. Pat. No. 5,250,236). SLN are loaded with hydrophilic or hydrophobic platinum compounds which may be dissolved in the internal phase of the microemulsions.

More particularly, the nanoparticles of platinum complexes of the invention are obtained by a process comprising:

a) preparing a first microemulsion by mixing a molten lipid, a surfactant, and optionally a co-surfactant and the platinum compound aqueous solution;

b) preparing a solution by mixing a surfactant and optionally a co-surfactant in water, heating to complete solution, preferably at the same melting temperature of the lipid used in a) and adding a co-surfactant;

c) dispersing the microemulsion obtained in a) into the solution obtained in b) obtaining a multiple microemulsion c);

d) dispersing the microemulsion obtained in c) in aqueous medium at a temperature ranging from 0.5° C. to 4° C. obtaining a dispersion of solid lipid microspheres;

e) washing with aqueous medium through ultrafiltration the obtained lipid microspheres obtained in d) and lyophilizing, optionally in the presence of a bulking agent and of a cryoprotecting agent.

Conventional bulking agents such as dextrane and the like may be advantageously used.

The lipid components employed according to the present invention are selected in the group comprising: triglycerides, such as for instance trilaurin, tripalmitin and tristearin, fatty acids such as lauric-, myristic-, palmitic and stearic acid; alcohols, such as myristyl-, cetylic-, stearyl alcohol. The surfactants are selected from the group comprising: sodium cholate, sodium deoxycholate, sodium glycolate, sodium taurocholate, sodium taurodesoxycholate, sodium bis(2-ethylhexyl)sulfosuccinate, lecithins and phospholipids, Polyoxyethylene Sorbitan Fatty Acid Esters (e.g. Tween 20, Tween 40, Tween 80), Sorbitan esters (Span 20, Span 40, Span 60, Span 80), ceramide, shingomyelin, galactocerebrosides, polyoxypropylene-polyoxyethylene glycol nonionic block co-polymer or a sucrose fatty ester. The co-surfactants are selected from the group comprising: low molecular weight alcohols or glycols, such as for instance isopropanol, butanol, hexanol, hexanediol, propyleneglycol, low molecular weight fatty acids, such as for instance butyric acid and hexanoic acid, esters of phosphoric acid and benzyl alcohol.

Stearic acid is preferred as lipid substance.

Preferred surfactants include soja phosphatidylcholine, sodium taurocholate and mixtures thereof.

Preferred co-surfactants comprise isopropanol. In the preparation of the microspheres according to the present invention the various substances are employed in the following proportions: the lipid components, which may contain drugs, between 4 and 25%, preferably 4 and 12% by weight of the total;

water, between 40 and 70%, preferably 55-65% by weight of the total;

surfactants between 8 and 30%, preferably between 12-22% by weight of the total;

co-surfactants 0-15%, preferably 6-12% by weight of the total.

The volume of water for the dispersion of the warm microemulsion is a 5 to 50 and preferably 5 to 20 volumes of water per volume of microemulsion.

The platinum compounds-SLN are of spherical shape, with average diameter between 70 and 200 nm, and are suitable to intravenous and oral administration.

Platinum compounds-SLN are absorbed through the lymph when administered by oral route. When administered intravenously, SLN are able to significantly alter the platinum compounds pharmacokinetics observed after administration of solution formulations. Moreover, SLN can enter into the tumor cells within a few minutes and are able to overcome physiological barriers as described in U.S. Pat. Nos. 6,238,694, 6,419,949.

Nanoparticles can be further elaborated to obtain stealth SLN, able to avoid reticular-endothelial system recognition, as described in U.S. Pat. No. 6,419,949.

The use of platinum compounds-SLN in anticancer therapy according to the invention provides the following advantages:

1. Improvement of oral bioavailability of poorly absorbed platinum compounds or of compounds unstable in the gut lumen;
2. Reduction of undesired interaction between the platinum compound and stomach/gut mucosa after oral administration, thus minimizing local toxicity;
3. Maximization of the oral bioavailability due to absorption of nanoparticles via the lymphatic system, with no hepatic first-pass effect;
4. Possibility to administer poorly water soluble platinum compounds by parenteral route;
5. Reduction of platinum compound-protein binding, and increase of the rate and extent of drug distribution;
6. Platinum compound protection from endogenous molecules in blood that may degrade/inactivate the compound before it gets to the tumor target;
7. Change of the pharmacokinetic profile of platinum compounds given intravenously by slowing down the drug release from the formulation and thus decreasing the peak concentrations and increasing the residence time in the systemic circulation;
8. Therapeutic index improvement by targeting to the tumor cells (enhanced permeability and retention effect), and gradual delivery of platinum compounds inside the cells with better anticancer efficacy;
9. Modification of the drug distribution pattern, including passage of the blood-brain barrier.

The platinum compounds-SLN of the invention may be administered to patients affected by cancer usually responsive to platinum compounds, suitably formulated in pharmaceutical formulations for oral and intravenous administration. Guidelines for the appropriate dosage regimens may be found in the above mentioned US patents disclosing platinum compounds.

EXAMPLES

Example 1

SLN of bis{trans(diammine)(chloro)platinum(II)}μ-(1,16-diamino-7,10-diazahexadecane-N1,N16) dinitrate salt. 2 $HNO_3$ Bis{trans(diammine)(chloro)platinum(II)}μ-(1,16-diamino-7,10-diazahexadecane-N1,N16) dinitrate salt. 2 $HNO_3$ of formula II (described in Example 17, page 15, line 25-31 of U.S. Pat. No. 6,022,892) is a potent bisplatinum complex endowed with outstanding antitumor activity in a variety of tumor cell lines. Nanoparticles of this compound were prepared with the procedure above described (U.S. Pat. No. 5,250,236) using lecithin, stearic acid, taurocholate, propionic acid, and an aqueous solution (0.01M NaCl, 0.01M HCl) of the bisplatinum compound). The warm microemulsion was dispersed in cold water (1-4° C.). Nanoparticles dispersion was repeatedly washed by ultrafiltration (100,000 Da cut-off) with distilled water.

HPLC and ICP analyses of the obtained bisplatinum complex-SLN demonstrated that more than 90% of the loaded bisplatinum complex was incorporated into the nanoparticles. SLN mean diameter was 120 nm as measured by Malvern Zetasizer 3000HS.

The platinum compound is stable in human plasma when incorporated in solid lipid nanoparticles and does not interact with plasma proteins. Bisplatinum compound-SLN is well tolerated when administered to CD1 mice and shows an improved therapeutic index when compared to aqueous solutions of the same compound.

Example 2

0.4 g stearic acid were melted at about 71° C. and 0.32 g soja phosphatidylcholine were added obtaining a hot clear solution. Then were added 260 μl of propionic acid and 200 μl of compound of Formula II in HCl 0,01 N aqueous solution (9 mg/ml) obtaining a clear microemulsion (micro 1).

Separately a solution of soja phosphatidylcholine (0.56 g), sodium taurocholate (0.67 g) and propionic acid (560 μl) in 4 ml of water was prepared and brought to 71° C. (solution 2).

Micro 1 is then poured in solution 2 obtaining a clear microemulsion at 71° C., which was then dispersed under stirring in 8 volumes water per volume of microemulsion at 1° C. obtaining a lipid nanosphere dispersion of 46 ml of volume.

At last, the dispersion was washed 3 times by tangential flow filtration using VIVAFLOW50 100 kDa cut off, each time adding 46 ml of water.

The nanospheres had an average diameter of 141 nm as measured by Malvern Zetasizer 3000HS and the polydispersion index was 0.36.

Example 3

0.36 g stearic acid, 0.36 g palmitic acid and 0.28 g soja phosphatidylcholine were melted at about 52° C. Then were added 400 μl of isopropyl alcohol and 0.12 g of sodium taurocholate. Then was added 400 μl of a solution of compound of Formula II in $H_2SO_4$ 0,05 mM aqueous solution (9 mg/ml) obtaining a clear microemulsion (micro 1).

Separately a solution of soja phosphatidylcholine (0.35 g), sodium taurocholate (1.2 g), isopropyl alcohol (800 μl) and 8 ml $H_2SO_4$ 0.05 mM aqueous solution, was prepared and brought to 52° C. (solution 2).

Micro 1 was then poured in solution 2 obtaining a clear microemulsion at 52° C., which was then dispersed under stirring in 10 volumes water per volume of microemulsion at 1° C. obtaining a lipid nanosphere dispersion of 96 ml of volume.

At last, the dispersion was washed 2 times by tangential flow filtration using PALL MINIMATE TFF Capsule 100 kDa cut off, each time adding 96 ml of HCl 0.032 mM aqueous solution.

After adding dextran (3 g for 100 ml of dispersion) the dispersion has been lyophilized.

The nanospheres obtained after the lyophilization process had an average diameter of 324 nm, as measured with Malvern Zetasizer 3000 HSA, and the polydispersion index was 0.5.

Example 4

0.40 g stearic acid and 0.28 g soja phosphatidylcholine were melted at about 72° C. Then were added 200 μl of isopropyl alcohol and 0.06 g of sodium taurocholate. Then was added 200 μl of compound of Formula II in $HNO_3$ 10 mM aqueous solution (9 mg/ml) obtaining a clear microemulsion (micro 1).

Separately a solution of soja phosphatidylcholine (0.35 g), sodium taurocholate (0.67 g) and isopropyl alcohol (400 μl) in 4 ml $HNO_3$ 10 mM aqueous solution, was prepared and brought to 72° C. (solution 2).

Micro 1 was then poured in solution 2 obtaining a clear microemulsion at 72° C., which was then dispersed under stirring in 6 volumes water per volume of microemulsion at 1° C. obtaining a lipid nanosphere dispersion, of 32 ml of volume.

At last, the dispersion was washed 2 times by tangential flow filtration using VIVAFLOW50, 100 kDa cut off, each time adding 32 ml of $HNO_3$ (1 mM) aqueous solution.

The nanospheres had an average diameter of 140 nm as measured with Malvern Zetasizer 3000 HSA and the polydispersion index was 0.26.

Example 5

0.40 g stearic acid and 0.32 g soja phosphatidylcholine were melted at about 70° C. Then were added 280 μl of octanoic acid and 0.04 g of sodium taurocholate. Then was added 200 μl of compound of formula II in HCl 0,01N aqueous solution (9 mg/ml) obtaining a clear microemulsion (micro 1).

Separately a solution of soja phosphatidylcholine (0.32 g), sodium taurocholate (0.66 g), octanoic acid (40 μl) and isopropyl alcohol (400 μl) and 4 ml of water, was prepared and brought to 70° C. (solution 2).

Micro 1 is then poured in solution 2 obtaining a clear microemulsion at 70° C., which was then dispersed under stirring in 8 volumes water per volume of microemulsion at 1° C. obtaining a lipid nanosphere dispersion of 44 ml of volume.

At last, the dispersion was washed 2 times by ultrafiltration with a 100 kDa cut off, each time adding 44 ml of water.

The nanospheres had an average diameter of 242 nm as measured with Malvern Zetasizer 3000 HSA and the polydispersion index was 0.20.

The invention claimed is:

1. Solid Lipid Nanoparticles comprising a hydrophilic platinum complex comprising anionic ligands and ligands containing amino groups.

2. The Solid Lipid Nanoparticles of claim 1, wherein the platinum complex is selected from the group consisting of trans-{bis[trans(diammine)(chloro)platinum (II) (μ-1,6-hexanediamine)]}diammineplatinum tetranitrate salt of formula I,

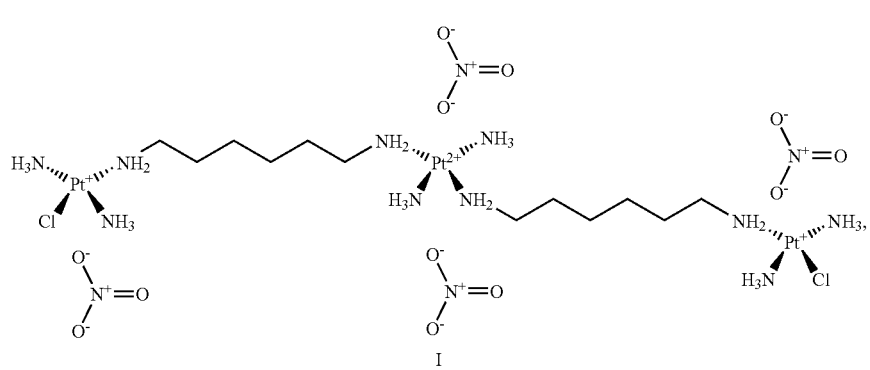

Formula I bis{trans(diammine)(chloro)platinum(II)}μ-(1,16-diamino-7,10-diazahexadecane-N1,N16) dinitrate salt 2HNO₃ of formula II, Formula II

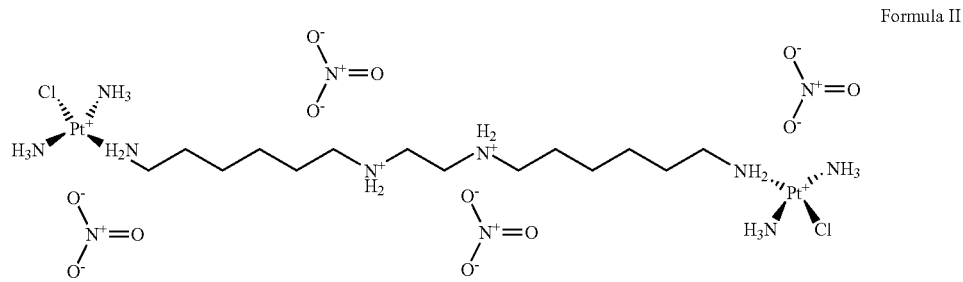

bis{trans(diammine)(chloro)platinum(II)}μ-(1,16-diamino-6,11-diazahexadecane-N1,N16) dinitrate salt 2HNO₃ of formula III, Formula III

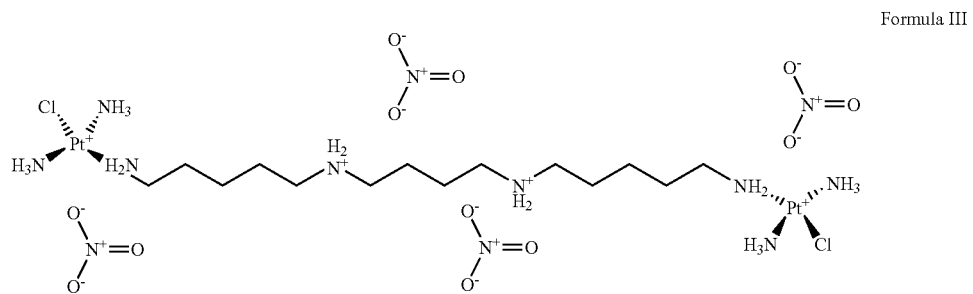

bis{trans(diammine)(chloro)platinum(II)}-μ-(1,12-diamino-4,9-diazadodecane-$N^1,N^{12}$) dinitrate salt 2HNO₃ of formula IV, Formula IV

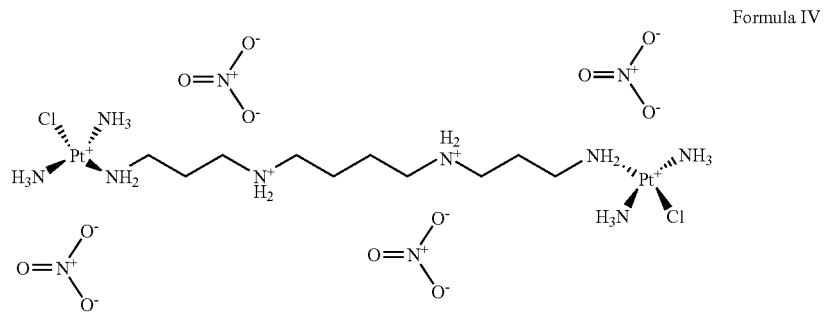

and bis{trans(diammine)(chloro)platinum (II)}-μ-(1,8-diamino-4-azaoctane-$N^1,N^8$) dinitrate salt HNO₃ of formula V Formula V

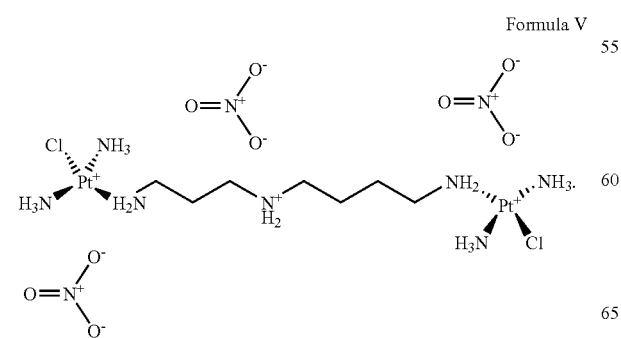

3. The Solid Lipid Nanoparticles of claim 1 obtainable by a process comprising:
   a. preparing a first microemulsion by mixing a molten lipid, a surfactant, and optionally a co-surfactant and an aqueous solution of the platinum complex;
   b. preparing a solution by mixing a surfactant and optionally a co-surfactant in water, heating to complete solution, preferably at the same melting temperature of the lipid used in a) and adding a co-surfactant;
   c. dispersing the microemulsion obtained in a) into the solution obtained in b) obtaining a multiple microemulsion c);
   d. dispersing the microemulsion obtained in c) in aqueous medium at a temperature ranging from 0.5° C. to 4° C. obtaining a dispersion of solid lipid microspheres; and
   e. washing with aqueous medium through ultrafiltration the obtained lipid microspheres obtained in d) and lyophilizing, optionally in the presence of a bulking agent and of a cryoprotecting agent.

4. A process for the preparation of the Solid Lipid Nanoparticles of claim 1, comprising:
  a. preparing a first microemulsion by mixing a molten lipid, a surfactant, and optionally a co-surfactant and an aqueous solution of the platinum complex;
  b. preparing a solution by mixing a surfactant and optionally a co-surfactant in water, heating, preferably at the same melting temperture of the lipid used in a) and adding a co-surfactant;
  c. dispersing the microemulsion obtained in a) into the solution obtained in b) obtaining a multiple microemulsion c);
  d. dispersing the microemulsion obtained in c) in aqueous medium at a temperature ranging from 0.5° C. to 4° C. obtaining a dispersion of solid lipid microspheres; and
  e. washing with aqueous medium through ultrafiltration the obtained lipid microspheres obtained in d) and lyophilizing, optionally in the presence of a bulking agent and of a cryoprotecting agent.

5. A pharmaceutical composition comprising the Solid Lipid Nanoparticles of claim 1.

6. A method of treating a patients affected by cancer sensitive to platinum complexes, which comprises administering to said patients a therapeutically effective amount of the Solid Lipid Nanoparticles of claim 1.

7. The Solid Lipid Nanoparticles of claim 1, formulated in an aqueous dispersion.

8. The Solid Lipid Nanoparticles of claim 1, which are lyophilized.

9. The Solid Lipid Nanoparticles of claim 3, wherein the surfactant is selected from the group consisting of soja phosphatidyl-chlorine, sodium taurocholate, and mixtures thereof.

10. The Solid Lipid Nanoparticles of claim 3, wherein the co-surfactant is isopropanol.

11. The pharmaceutical composition of claim 5, formulated for oral administration.

12. The pharmaceutical composition of claim 5, formulated for intravenous administration.

13. The method of claim 6, wherein the Solid Lipid Nanoparticles are administered orally.

14. The method of claim 6, wherein the Solid Lipid Nanoparticles are administered intravenously.

* * * * *

UNITED STATES PATENT AND TRADEMARK OFFICE
CERTIFICATE OF CORRECTION

PATENT NO. : 7,611,733 B2
APPLICATION NO. : 10/594003
DATED : November 3, 2009
INVENTOR(S) : Maria Rosa Gasco et al.

It is certified that error appears in the above-identified patent and that said Letters Patent is hereby corrected as shown below:

On the Title page of the patent:
(75) Inventors: "Turin (IT)" should read --Torino (IT)--.

Column 12, line 3, "patients" should read --patient--.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO.       : 7,611,733 B2  
APPLICATION NO.  : 10/594003  
DATED            : November 3, 2009  
INVENTOR(S)      : Maria Rosa Gasco et al.

Page 1 of 1

It is certified that error appears in the above-identified patent and that said Letters Patent is hereby corrected as shown below:

Column 12, line 11 "phatidyl-chlorine," should read --phatidyl-choline,--.

Signed and Sealed this  
Twenty-ninth Day of March, 2011

David J. Kappos  
*Director of the United States Patent and Trademark Office*